May 8, 1956 R. REGAN Plant Pat. 1,478
LANTANA PLANT
Filed June 7, 1955
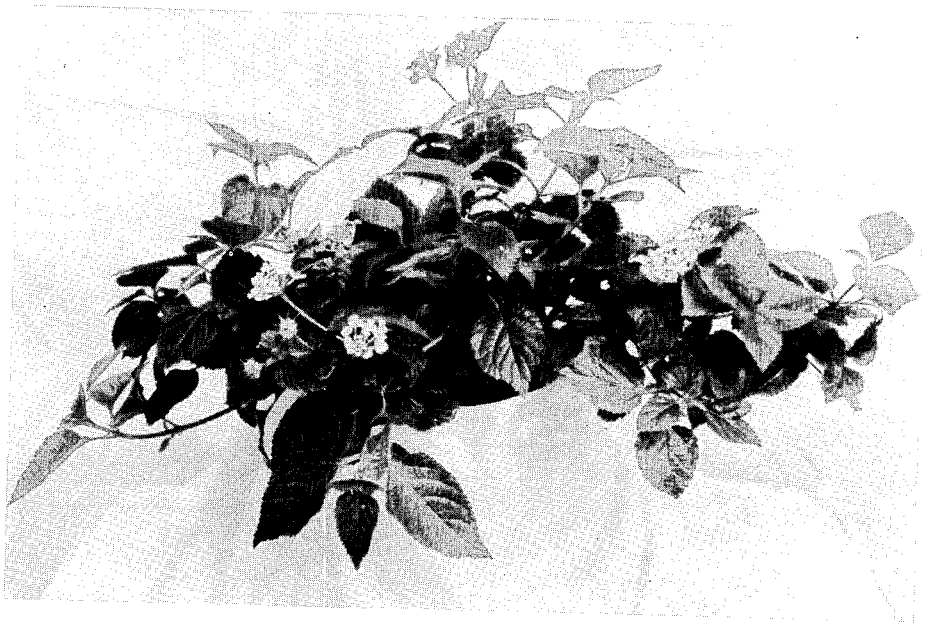
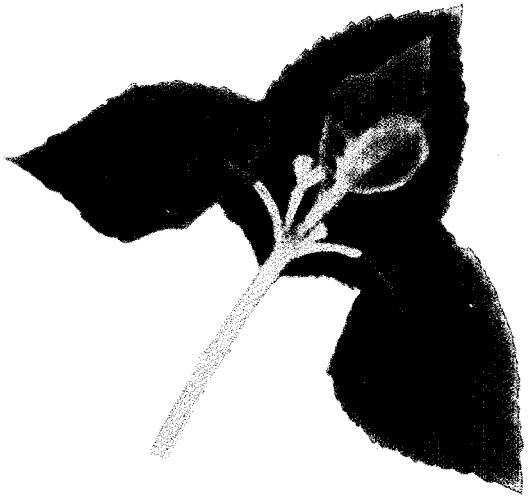
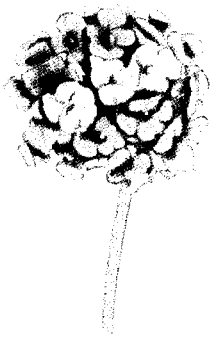
INVENTOR.
RONALD REGAN
BY J. F. Cuneo
ATTORNEY United States Patent Office Plant Pat. 1,478
Patented May 8, 1956

1,478

LANTANA PLANT

Ronald Regan, Monterey Park, Calif., assignor to Monrovia Nursery Co., Monrovia, Calif., a corporation of California Application June 7, 1955, Serial No. 513,924

1 Claim. (Cl. 47—60)

The present invention relates to a new and distinct variety of the lantana genus, which has resulted from cross breeding *Lantana callowiana* Goldrush, United States Plant Patent No. 1211 and *Lantana camara* Christine, an unpatented variety, after a considerable number of experiments conducted by me in Southern California, particularly Los Angeles County. Cross breeding the above named species of lantana has produced a new type as well as a new variety of lantana that combines some of the characteristics of each of the parent plants. The new variety of lantana differs in particular from its parent, *Lantana callowiana* Goldrush, in that its flowers can be described as predominantly phlox pink with a few of the centrally positioned florets shading to an orange buff, and the leaves are considerably larger. The novel plant differs from its other parent, *Lantana camara* Christine in that its growth is prostrate and the plant has many branches. The bloom of the new plant is made up of a number of florets in an umbel with the number of florets varying in each umbel.

The accompanying illustrations include a black and white photograph of the new phlox pink variety that clearly exhibits the plant's prostrate habit, which may be also described as trailing. The illustrations include also a full color reproduction of a single umbel as well as that of a leaf branch.

The new variety of lantana has been reproduced by me asexually in Southern California by means of cuttings, and it has been noted that the distinguishing characteristics are evident in the resulting plants and appear to be well established. This new variety cannot be reproduced by sexual means since the plant will not reproduce true from seed.

The following is a detailed description of the novel variety. All color names and numbers which are used in the description of the plant and flowers are based on the Horticultural Colour Chart adopted by the British Colour Council.

THE PLANT

*Nature and growth*

The plant is described as trailing and has many branches as shown in the accompanying photograph. The plant forms a prostrate, densely foliated shrub with vinelike stems up to three inches in length. The growth emanates from a central root.

*Stems*

The stems are slender and vinelike and are best described as woody.

*Leaves*

The foliage is persistent and ranges between moderately dense to very dense.

*Size.*—The leaves will average about one and one-half inches in width and about two and one-half inches in length.

*Shape.*—The leaves are described as broadly ovate, having serrated edges, with an apex that is acute-aristate; the base of the leaves being rounded.

*Arrangement.*—The leaves are opposite, the pairs alternating approximately 90° at about every two inches. The leaves are attached to the stem by a short peduncle.

*Color.*—Leek Green 000858.

*Appearance and texture.*—The surfaces of the leaves are sparsely pubescent, being slightly creased and having a leathery appearance. The ribs are quite prominent.

*Aroma.*—The leaves have a faint odor resembling somewhat the aroma of oil of eucalyptus.

*Blooming habit*

The plant is a profuse bloomer.

THE FLOWER

*Arrangement*

The flowers form in substantially hemispherical umbels which may vary between one inch and one and one-half inches in diameter. Each umbel may contain from ten to thirty individual florets, the average number of florets being about twenty-five. The umbels are produced on strong axillary peduncles, sometimes as long as three inches. The peduncles are slightly pubescent. All flowers form almost entirely on terminal growth.

*Florets*

The individual florets in the clusters are quite small.

*Color.*—Phlox Pink No. 625 for the majority of the florets with a few centrally positioned florets shading to Orange Buff No. 507/1.

*Corolla.*—Usually irregular consisting of two petals and two lobes.

*Aroma.*—The flowers have a faint aroma which is similar to that of the leaves, resembling somewhat the odor of oil of eucalyptus.

Having described my invention, I claim:

The new and distinct variety of lantana plant, substantially as herein shown and described, characterized especially by its abundance of faintly aromatic flowers and its combination of the prostrate, trailing growth habit of *Lantana callowiana* Goldrush, with the phlox pink flower coloring of *Lantana camara* Christine.

No references cited.